(12) United States Patent
Zhou et al.

(10) Patent No.: US 11,193,148 B2
(45) Date of Patent: Dec. 7, 2021

(54) METHOD FOR EXTRACTING ALPHA-KETOGLUTARATE AND PYRUVATE SIMULTANEOUSLY FROM MICROBIAL FERMENTATION BROTH OR ENZYMATIC CONVERSION SOLUTION

(71) Applicant: Jiangnan University, Wuxi (CN)

(72) Inventors: Jingwen Zhou, Wuxi (CN); Jian Chen, Wuxi (CN); Weizhu Zeng, Wuxi (CN); Guocheng Du, Wuxi (CN); Fang Fang, Wuxi (CN); Song Liu, Wuxi (CN)

(73) Assignee: Jiangnan University, Wuxi (CN)

( * ) Notice: Subject to any disclaimer, the term of this patent is extended or adjusted under 35 U.S.C. 154(b) by 331 days.

(21) Appl. No.: 15/654,487

(22) Filed: Jul. 19, 2017

(65) Prior Publication Data

US 2018/0105846 A1 Apr. 19, 2018

(30) Foreign Application Priority Data

Oct. 13, 2016 (CN) .......................... 201610893441.8

(51) Int. Cl.
| | | |
|---|---|---|
| *C07C 51/02* | (2006.01) | |
| *C07C 51/43* | (2006.01) | |
| *C07C 51/44* | (2006.01) | |
| *C07C 51/47* | (2006.01) | |
| *C07C 51/48* | (2006.01) | |
| *C12N 1/00* | (2006.01) | |
| *C12N 1/02* | (2006.01) | |
| *C12N 9/00* | (2006.01) | |
| *C12P 7/42* | (2006.01) | |
| *C12P 13/04* | (2006.01) | |
| *C12P 17/10* | (2006.01) | |
| *C12N 9/10* | (2006.01) | |

(52) U.S. Cl.
CPC ................ *C12P 7/42* (2013.01); *C07C 51/02* (2013.01); *C07C 51/43* (2013.01); *C07C 51/44* (2013.01); *C07C 51/47* (2013.01); *C07C 51/48* (2013.01); *C12N 1/02* (2013.01); *C12N 9/1096* (2013.01); *C12P 13/04* (2013.01); *C12P 17/10* (2013.01); *C12N 1/00* (2013.01); *C12N 9/00* (2013.01)

(58) Field of Classification Search
None
See application file for complete search history.

(56) References Cited

U.S. PATENT DOCUMENTS

2007/0031918 A1* 2/2007 Dunson, Jr. ............. C12M 27/02
435/41
2014/0356916 A1* 12/2014 Wittmann ................ C12N 9/93
435/115

OTHER PUBLICATIONS

Schugeri, K., Biotechnology: Bioprocessing, vol. 3, 2nd Edition, Chapter 21, pp. 558-592 (1993).*

(Continued)

*Primary Examiner* — Soren Harward
*Assistant Examiner* — Paul D Pyla
(74) *Attorney, Agent, or Firm* — IPro, PLLC

(57) ABSTRACT

The present disclosure provides a method for extracting alpha-ketoglutarate and pyruvate simultaneously from microbial fermentation broth or enzyme transformation solution, which is related to the technical field of biological separation and extraction. The method comprises the following steps: centrifuging the microbial fermentation broth or enzymatic conversion solution containing $\alpha$-KG and PA to remove the cells and other visible solids; removing the macromolecular impurities by ultrafiltration; evaporating and concentrating under reduced pressure conditions; extracting with the water-insoluble extraction after acidification; separating crude crystals of $\alpha$-KG and crude liquid of PA by evaporation crystallization method (if concentration of PA is great higher than that of $\alpha$-KG, crystallization separation should be conducted after distilling partial pure pyruvate); washing the crude crystal of $\alpha$-KG with water-insoluble organic solvent as ethyl acetate or butyl acetate, drying and crushing to obtain qualified $\alpha$-KG; distilling to gain qualified PA product applying high vacuum distillation (or molecular distillation).

8 Claims, 1 Drawing Sheet

(56) References Cited

OTHER PUBLICATIONS

Morgunov et al., Applied Microbiology and Biotechnology, vol. 97, No. 19, pp. 8711-8718 (2013).*
Chemical properties of α-Ketoglutarate and Pyruvate, accessed at SciFinder on Jun. 27, 2019 at https://scifinder.cas.org.*
Zeng et al., Bioprocess and Biosystems Engineering, vol. 41, pp. 1519-1527 (2018).*
Alkaya et al., .Chemosphere, vol. 77, pp. 1137-1142 (2009). (Year: 2009).*
Schugerl, K., Biotechnology: Bioprocessing, vol. 3, 2nd Edition, Chapter 21, pp. 558-592 (1993)(of record) (Year: 1993).*
Zhou et al., Letters in Applied Microbiology, vol. 51, pp. 264-271 (2010), (Year: 2010).*
Otto et al., Applied Microbiology Biotechnology, vol. 92, pp. 689-695 (2011). (Year: 2011).*
Zhou et al., Letters in Applied Microbiology, vol. 51, pp. 264-271 (2010) (of record). (Year: 2010).*
Otto et al., Applied Microbiology Biotechnology, vol. 92, pp. 689-695 (2011) (of record). (Year: 2011).*
Alkaya et al., .Chemosphere, vol. 77, pp. 1137-1142 (2009) (of record). (Year: 2009).*
Morgunov et al., Applied Microbiology and Biotechnology, vol. 97, No. 19, pp. 8711-8718 (2013) (of record). (Year: 2013).*
Chemical properties of α-Ketoglutarate and Pyruvate, accessed at SciFinder on Jun. 27, 2019 at https://scifinder.cas.org. (of record). (Year: 2019).*
Zeng et al., "Biosynthesis of keto acids by fed-batch culture of Yarrowia lipolytica WSH-Z06," Bioresource Tech., 243:1037-1043, 2017.

* cited by examiner

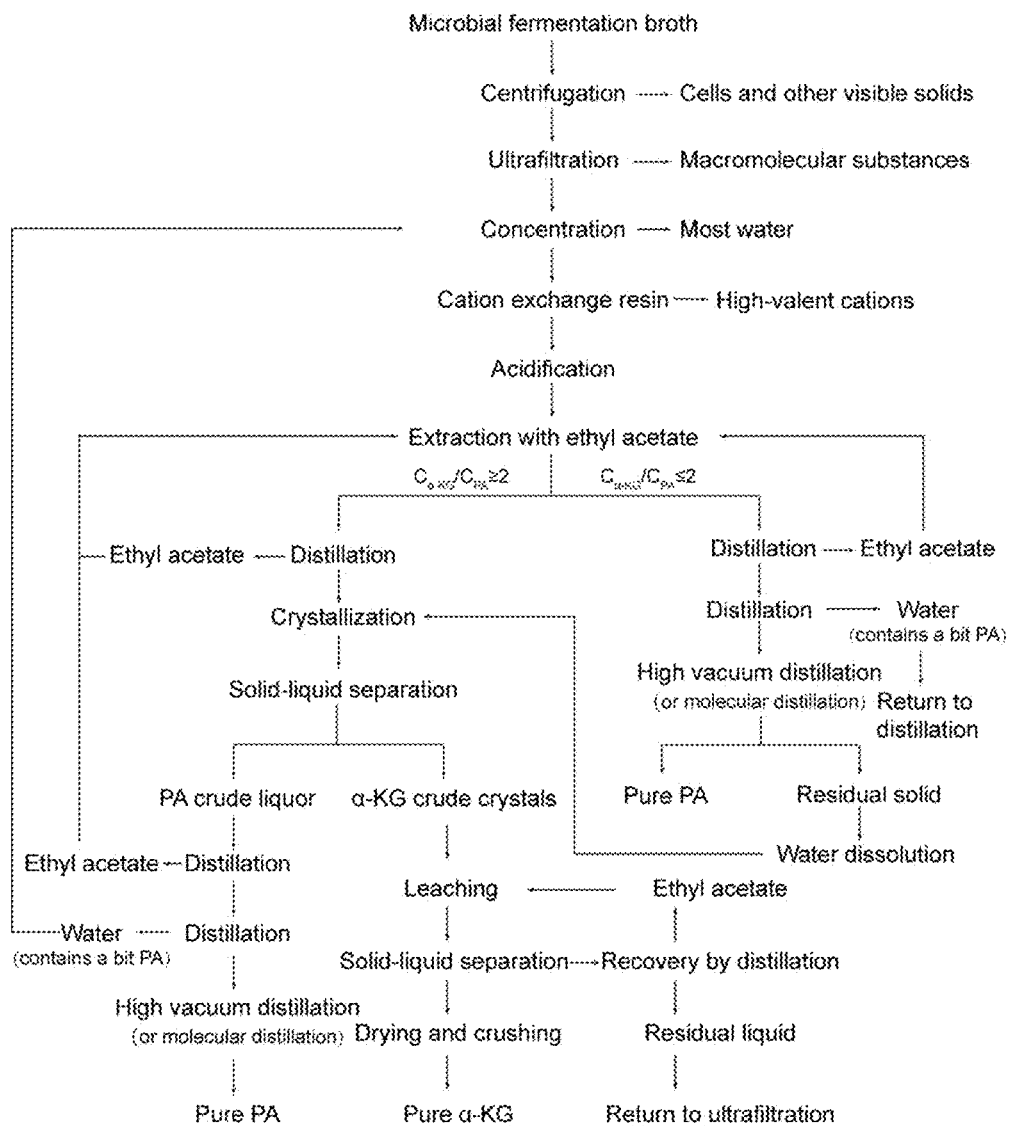

METHOD FOR EXTRACTING ALPHA-KETOGLUTARATE AND PYRUVATE SIMULTANEOUSLY FROM MICROBIAL FERMENTATION BROTH OR ENZYMATIC CONVERSION SOLUTION

CROSS-REFERENCES AND RELATED APPLICATIONS

This application claims the benefit of priority to Chinese Application No. 201610893441.8, entitled "A method for extracting alpha-ketoglutarate and pyruvate simultaneously from microbial fermentation broth or enzymatic conversion solution", filed Oct. 10, 2016, which is herein incorporated by reference in its entirety.

BACKGROUND OF THE INVENTION

Field of the Invention

The present invention relates to the field of biological separation and extraction, which particularly relates to a method for extracting alpha-ketoglutarate and pyruvate simultaneously from microbial fermentation broth or enzymatic conversion solution.

Description of the Related Art

Alpha-ketoglutaric acid (α-KG) is a pivotal intermediate in the tricarboxylic acid (TCA) cycle, and is a main precursor and intermediate in amino acid and protein metabolism. Pyruvate (PA) is also a metabolic intermediate that plays an important role in the metabolism of three major nutrients, which could achieve the interconversion of sugars, fats and amino acids in vivo by acetyl-CoA and TCA cycle. Both α-KG and PA are widely applied in scientific research, medicine, chemical, food industry and other fields.

Currently, most organic acids, like α-KG, PA and succinic acid, are produced by chemical synthesis routes and biotechnological routes. Biotechnological routes use microorganisms to produce targets by conversing the carbon sources. Methods of resin adsorption/desorption (such as extraction of itaconic acid, kojic acid and 2-keto-L-gulonic acid) and calcium salt precipitation (such as extraction of lactic acid and citric acid) are commonly employed to extract organic acids from fermentation broth in industry. However, it is not effective to separate α-KG and PA using the method of resin adsorption/desorption due to higher similarity between them. It could be theoretically possible to extract α-KG and PA simultaneously by applying the method of calcium salt precipitation based on different water solubility of the corresponding calcium salt. A series of polymers could be generated caused by PA polymerization under the condition of alkaline and heating in the process of calcium salt precipitation method, which seriously affects the extraction yield and product purity.

DETAILED DESCRIPTION

The goal of the present invention is to provide a method for extracting alpha-ketoglutarate and pyruvate simultaneously from microbial fermentation broth or enzymatic conversion solution, the wherein said method is conducting process of concentrating, acidifying, extracting, crystallizing, distilling and refining on microbial fermentation broth or enzymatic conversion solution containing α-KG and PA.

In one embodiment, the wherein said method comprises the following steps:

(1) Pretreatment of microbial fermentation broth or enzymatic conversion solution containing α-KG and PA: the microorganisms and other visible solids are separated from the microbial fermentation broth or enzymatic conversion solution containing α-KG and PA by centrifugal process. The macromolecular impurities are removed though filtration process. Making sure one of the organic acid α-KG or pyruvate concentration is ≥120 g/L by concentrating. And then, pretreatment solution is obtained after crossing the basic ion exchange resin to remove high-valent cations.

(2) Separation of crude α-KG and crude PA: the pretreatment solution should be acidified. α-KG and PA are extracted from acidified solution using water-insoluble extractive agent. On one hand, if $C_{\alpha\text{-}KG}:C_{PA} \geq 2$ of extraction solution, the extraction solution is further concentrated to a higher concentration of α-KG by evaporation, and the crude α-KG crystals and crude PA liquid are separated by centrifuging after crystallized at low temperature. On the other hand, if $C_{\alpha\text{-}KG}:C_{PA} \leq 2$ of extraction solution, the extractive agent and the dissolved water therein are removed by distillation, part of pure pyruvate could be harvested with further distillation, then a small amount of water is added to the residue of distillation, and the crude α-KG crystals and remaining crude PA liquid are separated by centrifuging after crystallized at low temperature.

(3) Purification of α-KG: the pure α-KG could be obtained after a series of steps conducting on the crude α-KG crystals, followed by leaching with water-insoluble organic solvent, drying and crushing.

(4) Purification of PA: the pure PA could be gained through distilling crude PA liquor under decompression conditions.

In one embodiment of the present disclosure, the wherein said separation and filtration includes one or more of centrifugation, ultrafiltration, microfiltration and frame filtration.

In one embodiment of the present disclosure, the wherein said acidification is to adjust the pH of solution ≤1.5.

In one embodiment of the present disclosure, the wherein said water-insoluble extractive agent is ethyl acetate or butyl acetate.

In one embodiment of the present disclosure, the wherein said extraction is performed at 5~40° C. for 10~60 min.

In one embodiment of the present disclosure, the wherein said crystallized at low temperature is crystallized at temperature ≤15° C.

In one embodiment of the present disclosure, the wherein said crude crystals and mother liquor were separated by centrifugation with centrifugal speed ≥2000 r/min.

In one embodiment of the present disclosure, the wherein said pure α-KG is obtained after a series of steps conducting on the crude α-KG crystals, followed by leaching with water-immiscible organic solvent, drying and crushing. The volume of water-immiscible organic solvent is ≤½-fold that of the crude α-KG crystals, and the drying temperature is 50~80° C.

In one embodiment of the present disclosure, the wherein said pure PA is gained by distilling crude PA liquor decompression conditions as −0.07~−0.1 Mpa at 30~60° C.

In one embodiment of the present disclosure, specific steps are as follows:

A: the microorganisms and other visible solids are separated from the microbial fermentation broth or enzymatic conversion solution containing α-KG and PA.

B: the macromolecular substances, such as cell fragments, pigments, lipids, proteins and polysaccharides, are removed from the above obtained supernatant, and then the residual filtrate is washed with a small amount of water, the wherein said ultrafiltration membrane module may be a roll membrane, a tubular membrane or a plate membrane with a molecular weight cut-off of 500~3,000.

C: one of the organic acid α-KG or pyruvate concentration is concentrated to be ≥120 g/L by decompression distillation at −0.07~−0.095 Mpa and 50~80° C.

D: the above concentrated solution is passed through the basic ion exchange resin to remove high-valent cations.

E: the above liquid obtained from step D is adjusted to pH≤1.5 by adding sulfuric acid while stirring.

F: the α-KG and PA is extracted by adding water-insoluble organic solvent to the above acidizing solution at 5~40° C. for 10~60 min, with the volume of the extractant is ≥2-fold that of the acidified solution, and the times of extraction is ≥2. On one hand, if $C_{\alpha\text{-}KG}:C_{PA}$ of the resulting extractant is ≥2, separation of α-KG and PA is carried out according to steps G-1 to K-1. On the other hand, if $C_{\alpha\text{-}KG}:C_{PA}$ of the resulting extractant is ≤2, separation of α-KG and PA is carried out according to steps G-2 to L-2.

G-1: the concentration of α-KG is concentrated to ≥200 g/L by distilling the water-immiscible extractant, such as ethyl acetate and butyl acetate, under conditions of −0.07~−0.095 Mpa and 35~60° C.

H-1: the concentrated liquid is rapidly cooled and crystallized at temperature ≤15° C. for 1 to 5 days, and then crude crystals of α-KG and crude liquid of PA are separated by centrifugation.

I-1: the crude crystals of α-KG obtained from the above step H-1 are washed with a water-immiscible organic solvent such as ethyl acetate or butyl acetate, and the volume of the water-insoluble organic solvent is ≤½-fold that of crude products. The pure α-KG is harvested after a series of steps conducting on the crude α-KG crystals, followed by leaching with water-insoluble organic solvent, drying under 50~80° C. condition and crushing into powder.

J-1: the crude PA is harvested by distilling off extractant and water therein from the crude liquid of PA gained from the above step H-1, under conditions of −0.07~0.095 Mpa and 35~60° C.

K-1: the pure PA is obtained by distilling the crude PA from above step applying high vacuum distillation or molecular distillation under conditions of −0.098~−0.1 Mpa and 25~60° C.

G-2: if the $C_{\alpha\text{-}KG}:C_{PA}$≤2 in the extractant obtained in step F, the extractant and the water therein are distilled off under the conditions of −0.07~−0.095 Mpa and 35~60° C.

H-2: partial pure PA is obtained by distilling the crude mixture of organic acid applying high vacuum distillation or molecular distillation under conditions of −0.098~−0.1 Mpa and 25~60° C.

I-2: the crude α-KG crystals and crude PA liquid are separated after adding a small amount of water to dissolve the residual solid completely from above distillation step and immediately crystallizing at low temperature, the wherein said crystallizing at low temperature is crystallizing at temperature ≤15° C. for 1~5 days.

J-2: the crude crystals of α-KG obtained from the above step I-2 are washed with a water-immiscible organic solvent such as ethyl acetate or butyl acetate, and the volume of the water-insoluble organic solvent is ≤½-fold that of crude products. The pure α-KG is harvested after a series of steps conducting on the crude α-KG crystals, followed by leaching with water-insoluble organic solvent, drying under 50~80° C. condition and crushing into powder.

K-2: the crude PA is harvested by distilling off extractant and water therein from the crude liquid of PA gained from the above step I-2, under conditions of −0.07~0.095 Mpa and 35~60° C.

L-2: the remaining pure PA is obtained by distilling the crude PA from above step with high vacuum distillation or molecular distillation under conditions of −0.098~−0.1 Mpa and 25~60° C.

Advantages of the present invention: the separation method could be effective to extract α-ketoglutarate and pyruvate from microbial fermentation broth or enzymatic conversion solution simultaneously. The purity of α-KG and PA was more than 99%, which met the food grade requirements. The extraction yield of α-KG and PA both reached to 80%, which improved obviously compared with traditional separation methods. Currently, the industrial standard of α-KG and PA is 98%, being worth 12,000~15,000 dollar/ton, while the food grade products with 99% purity are worth 20,000-23,000 dollar/ton, it is visible that this method of the present invention could bring higher economic benefits. This invention has the advantages of easy operation, high efficiency and low cost, and has great potential for industrial application.

BRIEF DESCRIPTION OF DRAWINGS

FIG. 1. Flow chart of extraction process in one embodiment of present disclosure which use ethyl acetate as extractant.

EXAMPLES

Determination of α-KG and PA

The concentrations of α-KG and PA are determined by high-performance liquid chromatography (HPLC) equipped with a Bio-Rad Aminex HPX-87H column, eluted with 5 mM $H_2SO_4$ at a flow rate of 0.5 mL/min and 40° C. α-KG and PA were detected by an Agilent 1260 (Agilent, Palo Alto, Calif., USA) UV absorbance detector at 210 nm.

Calculation of Purity $$W = \frac{f_2 \cdot m_1 \cdot p}{f_1 \cdot m_2}$$

$f_1$—peak area of standard sample solution determined by HPLC;
$f_2$—peak area of experimental sample solution determined by HPLC;
$m_1$—quality of standard sample (g);
$m_2$—quality of experimental sample (g);
p—purity of standard sample (%).

Calculation of Yield $$N = \frac{M \cdot W}{C \cdot V}$$

M—total quality of the obtained pure sample (g);
W—purity of the obtained sample (%);
C—concentration of the experimental sample in fermentation broth (g/L);
V—volume of the fermentation broth after removal of the cells (L).

The following examples are the method for simultaneous extraction of α-KG and PA from microbial fermentation broth or enzymatic conversion solution containing α-KG and PA. The fermentation broth was obtained by using *Yarrowia lipolytica* WSH-Z06 CCTCC M20714 or *Candida glabrata* CCTCC M202019 as fermented strain respectively.

Other similar microbial fermentation broth or enzymatic conversion solution containing α-KG and PA could be carried out according to the embodiment of the present invention, and the high purity of α-KG and PA also could be obtained through simple modification.

The present disclosure was described in detail referencing to the accompanying drawings.

Example 1

Extraction of α-KG and PA from the fermentation broth obtained by using *Y. lipolytica* WSH-Z06 as fermented strain was carried out as the following steps:

(1) Centrifugation filtration: the fermentation broth containing α-KG and PA was centrifuged to remove cells and other visible solids, with the centrifuge conditions of room temperature and 3,000 r/min.

(2) Membrane filtration: the macromolecular substances, such as cell fragments, pigments, lipids, proteins and polysaccharides, were removed from the above obtained supernatant with ultrafiltration membrane module, and then the residual filtrate was washed with a small amount of water to increase the yield of extraction. The applied ultrafiltration membrane module was a roll membrane with a molecular weight cut-off of 500~3,000, and the ultrafiltration process was conducted under the conditions of room temperature and operating pressure of 4~10 Bar.

(3) Concentration: the concentration of α-KG was concentrated to 120 g/L by distilling the obtained ultrafiltrate under reduced pressure condition of −0.08 Mpa at 65° C.

(4) Removal of impurities by ion exchange resin: The concentrated solution flowed through 732 cation exchange resin, which was pre-acidified to pH 2.0 and washed to neutral (sodium resin was converted to hydrogen type resin). The purpose of this operation is to remove high-valent cations from the concentrated solution and acidify the solution at the same time.

(5) Acidification: the pH of concentrated liquor gained after ion exchange column treatment was adjusted to 1.5 by adding sulfuric acid with stirring under normal temperature condition.

(6) Extraction: 3-fold volume of ethyl acetate that of acidified solution was used to extracted organic acids at 15° C. for 20 min, and then the aqueous and organic phases were separated. This extraction experiments were repeated 3 times. The $C_{\alpha\text{-}KG}:C_{PA}$ of the resulted solution was 2.

(7) Distillation: The extractant ethyl acetate containing organic acid obtained from the extraction process was distilled under reduced pressure of −0.08 Mpa at 50° C. until the concentration of α-KG increased to 200 g/L.

(8) Separation of α-KG crude crystals and PA crude liquor: the crude α-KG crystals and crude PA liquid are separated after distilling off extractant ethyl acetate to thick liquid of organic acid mixture and immediately crystallizing at 10° C. for 1 day. The crystal is cultured for one day and then separated from mother liquor by centrifugation.

(9) Obtainment of pure α-KG: The α-KG crude crystal was washed with ethyl acetate, of which the volume is ¼-fold than that of crude crystal. After removing the ethyl acetate by centrifugation and drying at 65° C. in a constant temperature drying oven, the pure α-KG was collected. The yield of this procedure was 79.8% and the purity of α-KG was 99.3%.

(10) Harvest of crude PA: the PA crude liquor was distilled to remove ethyl acetate under reduced pressure of −0.09 Mpa at 40° C. and then temperature was raised to 55° C. to distill off the water therein.

(11) Obtainment of pure PA: The pure PA, light yellow transparent liquid, was obtained with high vacuum distillation at −0.099 Mpa and 50° C. For liquid product of PA, the purity gradually decreases as the color of the liquid changes from a light yellowish transparent to a yellowish transparent to a red transparent, then to a reddish viscous. The yield of this procedure was 80.6% and the purity of PA was 99.5%.

Example 2

The embodiment is the same as Example 1 except that the $C_{\alpha\text{-}KG}:C_{PA}$ of the resulted solution in step (6) was 3.5 and step (4) was not performed.

The content of α-KG and PA was determined. The purity of α-KG was 97.8% and its yield was 80.4%. The purity of PA was 99.5% and its yield was 72.7%.

Example 3

Taking the fermentation broth obtained from *Y. lipolytica* WSH-Z06 as fermented strain ($C_{\alpha\text{-}KG}:C_{PA}$=3.5), The embodiment is the same as Example 1 except that the $C_{\alpha\text{-}KG}:C_{PA}$ of the resulted solution in step (6) was 3.5 and the step (2) is not carried out. The centrifuged liquid obtained in step 1 was distilled under the conditions of step (3) directly.

The content of α-KG and PA was determined. The purity of α-KG was 96.2% and its yield was 81.7%. The purity of PA was 99.3% and its yield was 65.2%.

Example 4

The embodiment is the same as Example 1 except that the $C_{\alpha\text{-}KG}:C_{PA}$ of the resulted solution in step (6) was 3.5 and the pH of concentrated solution was adjusted to 3 in the step (5).

The content of α-KG and PA was determined. The purity of α-KG was 99.2% and its yield was 45.8%. The purity of PA was 99.3% and its yield was 40.9%.

Example 5

The embodiment is the same as Example 1 except that the $C_{\alpha\text{-}KG}:C_{PA}$ of the fermentation culture was 3.5 and step (6) is not carried out.

The content of α-KG and PA was determined. The purity of α-KG was 99.4% and its yield was 52.8%. The purity of PA was 99.6% and its yield was 56.3%.

Example 6

Taking the fermentation broth obtained from *Y. lipolytica* WSH-Z06 as fermented strain ($C_{\alpha\text{-}KG}:C_{PA}$=3.5), The embodiment is the same as Example 1 except that the $C_{\alpha\text{-}KG}:C_{PA}$ of the resulted solution in step (6) was 3.5 and the extraction (step 6) and the purification (step 9) were carried out using butyl acetate instead of ethyl acetate.

The content of α-KG and PA was determined. The purity of α-KG was 99.4% and its yield was 82.1%. The purity of PA was 99.6% and its yield was 79.8%.

Example 7

Extraction of α-KG and PA from the fermentation broth obtained by using *C. glabrata* as fermented strain was carried out as the following steps:

(1) Centrifugation filtration: the fermentation broth containing α-KG and PA was centrifuged to remove cells and other visible solids, with the centrifuge conditions of room temperature and 3,000 r/min.

(2) Membrane filtration: the macromolecular substances, such as cell fragments, pigments, lipids, proteins and polysaccharides, were removed from the above obtained supernatant with ultrafiltration membrane module, and then the residual filtrate was washed with a small amount of water to enhance the yield of extraction. The applied ultrafiltration membrane module was a roll membrane with molecular weight cut-off of 500~3,000, and the ultrafiltration process was conducted under the conditions of room temperature and operating pressure of 4~10 Bar.

(3) Concentration: the concentration of PA was concentrated to 200 g/L by distilling the obtained ultrafiltrate under reduced pressure condition of −0.08 Mpa at 65° C.

(4) Removal of impurities by ion exchange resin: The concentrated solution flowed through 732 cation exchange resin, which was pre-acidified to pH 2.0 and washed to neutral (sodium resin was converted to hydrogen type resin). The purpose of this operation is to remove high-valent cations from the concentrated solution and acidify the solution at the same time.

(5) Acidification: the pH of concentrated liquor gained after ion exchange column treatment was adjusted to 1.0 by adding sulfuric acid with stirring under normal temperature condition.

(6) Extraction: Ethyl acetate was used to extracted organic acids at 35° C. for 15 min and the volume of ethyl acetate was 5-fold than that of acidified solution. The aqueous and organic phases were separated after extraction. This extraction experiments were repeated 2 times. The $C_{\alpha-KG}:C_{PA}$ of the resulted solution was 0.5.

(7) Distillation off ethyl acetate and water: the extractant was firstly distilled off under the conditions of −0.08 Mpa at 50° C. to remove ethyl acetate and then distilled at −0.09 Mpa and 53° C. remove water.

(8) Obtainment of partial pure PA: partial pure PA is obtained by distilling the organic acid mixture under −0.099 Mpa and 30° C.

(9) Separation of α-KG crude crystals and PA crude liquor: a small amount of water was added to dissolve the residual solid completely, and then the mixture immediately crystallized at 10° C. for 2 days. After crystallization, the crude α-KG crystals and crude PA liquid are separated.

(10) Obtainment of pure α-KG: The α-KG crude crystal was washed with ethyl acetate, of which the volume is ½-fold than that of crude crystal. Then the pure α-KG was obtained after removing the ethyl acetate by centrifugation, drying at 65° C. and crushing into powder.

The yield of this procedure was 80.9% and the purity of α-KG was 99.4%.

(11) Harvest of crude PA: the PA crude liquor was firstly distilled at 0.09 Mpa and 40° C. to remove ethyl acetate and then distilled at 55° C. to remove water.

(12) Obtainment of remaining pure PA: The pure PA, light yellow transparent liquid, was obtained by distilling crude PA employing molecular distiller under conditions of −0.099 Mpa and 30° C. The yield of this procedure was 82.8% and the purity of PA was 99.6%.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for simultaneously extracting alpha-ketoglutarate (α-KG) and pyruvate (PA) from a single fermentation broth or enzymatic conversion solution, wherein said method comprises:

(A) fermenting a single strain of yeast to produce α-KG and PA in a single microbial fermentation broth;

(B) pretreating the single microbial fermentation broth or an enzymatic conversion solution comprising both α-KG and PA by:

centrifuging and separating microorganisms and other visible solids from the microbial fermentation broth or enzymatic conversion solution to obtain a supernatant, removing macromolecular impurities though a filtration process by filtering the supernatant through an ultrafiltration membrane module to remove macromolecular substances, cell fragments, pigments, lipids, proteins, and polysaccharides, and washing residual filtrate with a small amount of water, wherein the ultrafiltration membrane module is selected from the group consisting of: a roll membrane, a tubular membrane, and a plate membrane with molecular weight cut-off of 500 to 3,000 Daltons, concentrating α-KG and PA to a concentration of ≥120 g/L by decompression distillation at −0.07 to −0.095 Mpa and at a temperature of 50° C. to 80° C., and separating the concentrated α-KG and PA by basic ion exchange resin chromatography to remove high-valent cations thereby obtaining a pretreatment solution;

(C) separating crude α-KG and crude PA by acidifying the pretreatment solution to obtain an acidified solution, wherein acidifying the pretreatment solution further comprises adjusting the pH of the pretreatment solution to be ≤1.5 by adding sulfuric acid while stirring;

(D) extracting α-KG and PA to obtain an extraction solution from the acidified solution using a water-insoluble extractive agent by adding the water-insoluble organic solvent at 5° C. to 40° C. for 10 to 60 minutes, while maintaining a volume of extractant of ≥2-fold that of the acidified solution, and wherein extraction is repeated two more times;

(E) determining a ratio of α-KG concentration to PA concentration in the extraction solution; wherein if $C_{\alpha-KG}:C_{PA}$ is between 2 and 3.5 in the extraction solution, then separating α-KG and PA by steps G-1 to K-1:

G-1: further concentrating the extraction solution to obtain a higher concentration of α-KG by evaporation by concentrating α-KG to a concentration of ≥200 g/L by distilling a water-immiscible extractant, wherein the water-immiscible extractant is ethyl acetate or butyl acetate, under conditions of −0.07 to −0.095 Mpa and 35° C. to 60° C., and H-1: cooling the concentrated liquid from step G-1 rapidly and crystallizing at low temperature of ≤15°

C. for 1 to 5 days, and separating the crude α-KG crystals and crude PA liquid by centrifuging after crystallization;

I-1: washing crude crystals of α-KG obtained from the step H-1 with the water-immiscible organic solvent, wherein the water immiscible organic solvent is ethyl acetate or butyl acetate, with a volume of the water-immiscible organic solvent to be ≤½-fold of that of crude products; and harvesting the α-KG by leaching with the water-immiscible organic solvent, drying at a temperature of 50° C. to 80° C., and crushing into powder;

J-1: harvesting crude PA by distilling off extractant and water therein from liquid of PA gained from the step H-1, under conditions of −0.07 to −0.095 Mpa and at a temperature of 35° C. to 60° C.;

K-1: obtaining pure PA by distilling the pyruvate from the above steps by applying a high vacuum distillation or molecular distillation under conditions of −0.098 to −0.1 Mpa and at a temperature of 25° C. to 60° C.;

wherein if $C_{\alpha\text{-}KG}{:}C_{PA}$ is less than 2 in the extraction solution, then:

removing the extractive agent and the dissolved water therein by distillation, harvesting part of a pure PA with further distillation, adding a small amount of water to a residue of distillation, and separating crude α-KG crystals and remaining crude PA liquid by centrifuging after crystallization at low temperature; and (F) purifying PA by distilling crude PA liquid under decompression conditions.

2. The method of claim 1, wherein pretreating the microbial fermentation broth or the enzymatic conversion solution further comprises one or more of: centrifugation, ultrafiltration, microfiltration, and filtration.

3. The method of claim 1, wherein the water-insoluble extractive agent is ethyl acetate or butyl acetate.

4. The method of claim 1, further comprising:

determining a ratio of α-KG concentration to PA concentration in the extraction solution; wherein if $C_{\alpha\text{-}KG}{:}C_{PA}$ is less than 2, then G-2: distilling off the extractant and water therein at −0.07 to −0.095 Mpa and 35 to 60° C.;

H-2: obtaining a partial pure pyruvate by applying a high vacuum distillation or molecular distillation under conditions of −0.098 to −0.1 Mpa and 25 to 60° C.;

I-2: separating crude α-KG crystals and crude pyruvate liquid after adding water to dissolve any residual solids completely and crystallizing at a temperature of 15° C. for 1 to 5 days;

J-2: obtaining the crude crystals of α-KG from the above step I-2 by washing with a water-immiscible organic solvent of ethyl acetate or butyl acetate, at a volume of ½-fold that of crude products; and harvesting pure α-KG after leaching with water-insoluble organic solvent, drying at 50 to 80° C., and crushing into powder;

K-2: harvesting crude pyruvate by distilling off extractant and water therein from the crude pyruvate gained from the step I-2, at −0.07 to 0.095 Mpa and 35 to 60° C.;

L-2: obtaining pure pyruvate by distilling the crude pyruvate from the step K-2 with high vacuum distillation or molecular distillation at −0.098 to −0.1 Mpa and 25 to 60° C.

5. The method of claim 1, wherein the extraction is performed on the single microbial fermentation broth produced by the single strain of yeast, and wherein the single strain of yeast is a single strain of *Yarrowia lipolytica* or a single strain of *Candida glabrata*.

6. The method of claim 5, wherein the extraction is performed on the single microbial fermentation broth produced by the single strain of *Yarrowia lipolytica*, which is *Yarrowia lipolytica* WSH-Z06 (CCTCC M20714).

7. The method of claim 5, wherein the extraction is performed on the single microbial fermentation broth produced by the single strain of *Candida glabrata*, which is *Candida glabrata* CCTCC M202019.

8. The method of claim 1, wherein if $C_{\alpha\text{-}KG}{:}C_{PA}$ is less than 0.5 in the extraction solution, then the following steps are taken in step (E):

removing the extractive agent and the dissolved water therein by distillation, harvesting part of a pure PA with further distillation, adding a small amount of water to a residue of distillation, and separating crude α-KG crystals and remaining crude PA liquid by centrifuging after crystallization at low temperature.

* * * * *